United States Patent [19]

Belknap

[11] Patent Number: 5,366,464
[45] Date of Patent: Nov. 22, 1994

[54] ATHERECTOMY CATHETER DEVICE

[76] Inventor: John C. Belknap, 1740 Amherst St., Buffalo, N.Y. 14214

[21] Appl. No.: 95,946

[22] Filed: Jul. 22, 1993

[51] Int. Cl.[5] .............................. A61B 17/22
[52] U.S. Cl. ........................ 606/159; 606/171
[58] Field of Search ............ 606/159, 170, 171, 169; 604/22; 128/751, 752; 15/104.05

[56] References Cited

U.S. PATENT DOCUMENTS

| | | | |
|---|---|---|---|
| 4,020,847 | 5/1977 | Clark | 128/751 X |
| 4,445,509 | 5/1984 | Auth | 128/305 |
| 4,653,496 | 3/1987 | Bundy et al. | 606/159 |
| 4,685,458 | 8/1987 | Leckrone | 606/159 X |
| 4,771,774 | 9/1988 | Simpson et al. | 128/305 |
| 4,781,186 | 11/1988 | Simpson et al. | 606/171 |
| 4,979,951 | 12/1990 | Simpson | 606/159 |
| 5,154,724 | 10/1992 | Andrews | 606/159 |

FOREIGN PATENT DOCUMENTS

665908 6/1979 U.S.S.R. .

Primary Examiner—Michael H. Thaler
Attorney, Agent, or Firm—Joseph P. Gastel

[57] ABSTRACT

An atherectomy catheter device including a flexible casing, an elongated flexible tubular coil in the casing, a window extending axially in the flexible tubular coil and casing for placement in contiguous relationship to a lesion in a blood vessel, a cutting edge on the coil in the window, and an actuator having structure therein for both rotating and reciprocating the catheter to cause the cutting edge to excise the lesion from the blood vessel. The elongated tubular member may be a flexible corrugated member. An atherectomy catheter including a flexible casing, an elongated flexible tubular coil in the casing, a window extending axially in the flexible tubular coil and casing, a rotatable knife member in the flexible coil, and a drive for rotating and advancing the knife axially through the window.

18 Claims, 6 Drawing Sheets

ATHERECTOMY CATHETER DEVICE

BACKGROUND OF THE INVENTION

The present invention relates to improved atherectomy catheter devices.

In U.S. Pat. No. 4,781,186 there are disclosed flexible atherectomy catheters which are used to excise lesions in arterial vessels. Each of these catheters include a window which is positioned in facing relationship to the lesion. A balloon is located on the catheter in diameterically opposed relationship to the window to force the catheter toward the lesion and thus cause it to enter the window. Thereafter, a blade within the catheter is passed axially by the window to excise the lesion within the catheter. However, the window portion of the catheter is not flexible so as to permit it conform to the curvature of an artery.

SUMMARY OF THE INVENTION

It is accordingly the primary object of the present invention to provide an improved atherectomy catheter having a distal end portion which is flexible and thus can efficiently follow the curvature of curved blood vessels.

Another object of the present invention is to provide a flexible atherectomy catheter which not only can conform the shape of curved blood vessels but also has an unique cutting edge which can flex with the flexible catheter and cut lesions in all orientations thereof.

A further object of the present invention is to provide a flexible catheter having a flexible serrated cutting edge which can not only cut relatively soft lesions as it is reciprocated across them, but, because of its unique serrated cutting edge, can also cut hard lesions which have high density calcium therein.

Another object of the present invention is to provide an improved atherectomy catheter which can conform to a curved blood vessel and which contains a separate cutting blade which can follow the changing curvature of the catheter as it traverses a blood vessel.

Yet another object of the present invention is to provide an improved atherectomy catheter device which can follow the curvature of a blood vessel to exise a lesion therein and which also includes structure for conducting dye to the site of the lesion.

Still another object of the present invention is to provide an atherectomy device including a flexible catheter and a drive mechanism for both rotating the catheter and reciprocating it. Other objects and attendant advantages of the present invention will readily be perceived hereafter.

The present invention relates to an atherectomy catheter comprising elongated flexible tubular means for placement next to a lesion in a blood vessel, window means defining an opening in said elongated flexible tubular means for receiving said lesion, an edge portion on said window means, and cutting edge means on said edge portion for excising said lesion which enters said window means.

The present invention also relates to an atherectomy catheter device as set forth in the immediately preceding paragraph including means for both rotating and reciprocating the flexible tubular means.

The present invention also relates to a flexible atherectomy catheter for excising a lesion in a blood vessel comprising an elongated flexible tubular casing, an elongated flexible tubular coil in said casing, and a window extending through both said elongated flexible coil and said elongated flexible casing for receiving said lesion.

The present invention also relates to a flexible tube for use at the site of an atherectomy comprising a flexible coil, a first opening in said coil, a flexible casing surrounding said coil proximate said opening, and a second opening in said casing overlapping said first opening.

The present invention also relates to an atherectomy catheter comprising a flexible coil, a first opening in said coil, a flexible casing surrounding said coil proximate said opening, and a second opening in said casing overlapping said first opening, and a movable cutter in said coil for movement past said first and second openings.

The present invention also relates to an atherectomy device comprising an atherectomy catheter including an elongated flexible coil, a flexible casing on said coil, a first opening in said coil, a second opening in said casing overlapping said first opening, a dye-carrying lumen in said coil, a guide wire in said lumen, a drive motor for reciprocating and rotating said atherectomy catheter, and means for injecting dye into said dye-carrying lumen.

The various aspects of the present invention will be more fully understood when the following portions of the specification are read in conjunction with the accompanying drawings wherein:

BRIEF DESCRIPTION OF THE DRAWINGS

FIG. 11 is a fragmentary side elevational view taken substantially in the direction of arrows 11—11 of FIG.

9 and showing the cutting edge configuration of the catheter;

FIG. 14 is a fragmentary side elevational view, partially in cross section, showing an arrangement for injecting contrast dye into the catheter;

FIG. 15 is a fragmentary enlarged portion of FIG. 14;

FIG. 16 is a cross sectional view of a flexible atherectomy catheter which is formed from flexible corrugated tubing;

FIG. 17 is a fragmentary view, partially in cross section, taken substantially in the direction of arrows 17—17 of FIG. 16.

DESCRIPTION OF THE PREFERRED EMBODIMENTS

Summarizing briefly in advance, the improved atherectomy catheter device 10 includes a flexible atherectomy catheter 11, a drive unit D therefor, which is utilized to rotate and reciprocate the catheter, and associated structure.

Figure 4:
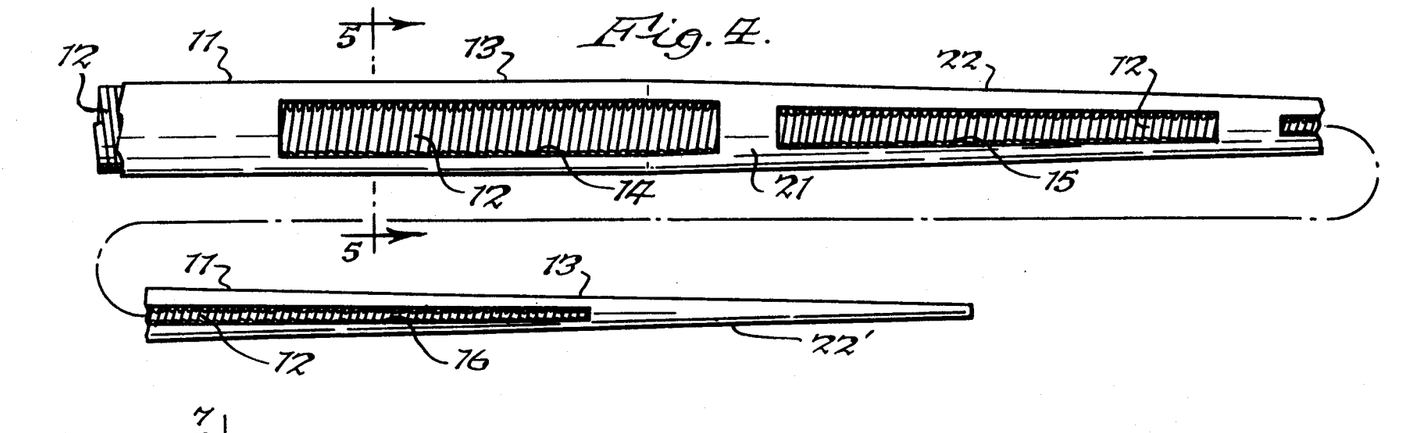
FIG. 4 is an enlarged fragmentary view of the flexible distal end portion of a catheter formed from a coil of wire within a casing and having a tapered end with different sized windows providing different cutting areas.
Figure 5:
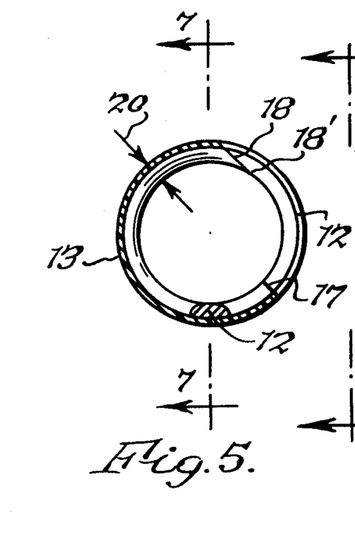
FIG. 5 is a cross sectional view taken substantially along line 5—5 of FIG. 4 and showing the cutting edge on the window of the catheter.
Figure 6:
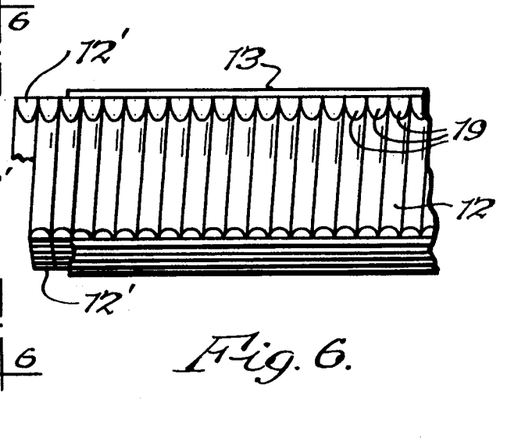
FIG. 6 is a fragmentary side elevational view taken substantially in the direction of arrows 6—6 of FIG. 5 and showing primarily the serrated-like cutting edge configuration of the cutting edge.
Figure 7:
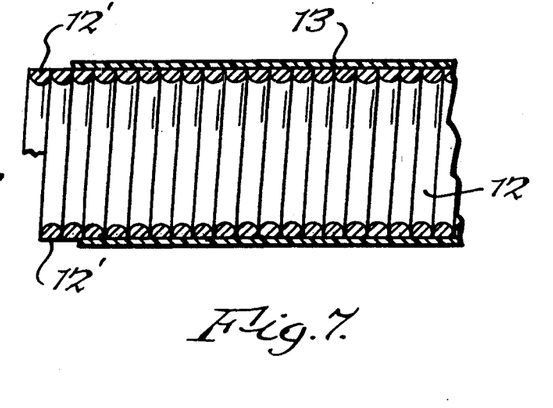
FIG. 7 is a fragmentary cross sectional view taken substantially along line 7—7 of FIG. 5 and showing the coil portions of the catheter which do not include a window.

One embodiment of the flexible catheter 11 is shown in FIGS. 4-7, and it essentially comprises a length of flexible coiled wire 12 encased in a flexible plastic sheath 13 which may be molded thereabout or mounted thereon. Sheath 13 may be made of a suitable flexible plastic such as polyethylene or polypropylene or any other suitable material which is sufficiently flexible to permit the required flexing of the distal end of the catheter. In this embodiment the outer surface 12' (FIGS. 6 and 7) of the flexible coil 12 has been centerless ground to provide a relatively smooth surface onto which the plastic sheath 13 is applied. In the embodiment of FIG. 4, the end of the catheter is tapered, and a plurality of windows 14, 15 and 16 of progressively smaller sizes are cut through sheath 13 and the wire coil 12. As can be seen from FIG. 5, the edge 18 is cut at a slant to produce a cutting edge 18'; and because of the inherent structure of coil 12, the edge 18' comprises a plurality of serrations 19 (FIG. 6). Furthermore, the circumferential opening dimension of window 14 is between edge 17 and edge 18' (FIG. 5), and this circumferential opening is less than 360° of the circumference of the catheter, and preferably less than 180° of the circumference of the catheter. In use, when the catheter is rotated, the amount which is sliced from the lesion will be as set forth by dimension 20, that is, the combination of the thickness of casing 13 and the thickness of wire coil 12. Thus, when catheter 11 is rotated within a vessel, cutting edge 18' can get no closer to the vessel wall than the combined thickness of casing 13 and wire coil 12.

As can be seen from FIG. 4, there are a plurality of windows 14, 15 and 16 and that the portions of the catheter to the right of window 14 are tapered. Thus, to the right of portion 21 between windows 14 and 15, the outer surface 22 is of constantly decreasing dimension. Furthermore, window 15 is circumferentially smaller than window 14, and window 16 is circumferentially smaller than window 15. The structure of the cutting edge 24 in window 15 is the same as the structure of cutting edge 18 of window 14. Also, the structure of the cutting edge 26 in window 16 is the same as the structure of the cutting edge 18 of window 14. The reason that the end of the catheter is tapered is so that the tip can be used for cutting in smaller vessels. It will be appreciated, however, if desired, the catheter can have only a single window of a predetermined size in the end thereof which is located in the uniform diameter section in which window 14 of FIG. 4 is located and extends into the distal tapered end of the catheter. In this respect, the window can be of a uniform circumferential dimension throughout its length with the dimension being such that it fits into the smallest portion of the tapered end portion. Also, it will be appreciated that catheters of different sizes can be used for different vessels. It will also be appreciated that only the distal end of the catheter need be of the described construction of a flexible coil and flexible casing, while the remaining portion of the catheter leading toward the drive unit D can merely be a flexible tube. The wire in the embodiments of FIGS. 4-7 is continuous and of uniform constant size throughout, but the coil is tapered to fit into the tapered end of the catheter.

Figures 8, 9, 10, 12, 13:
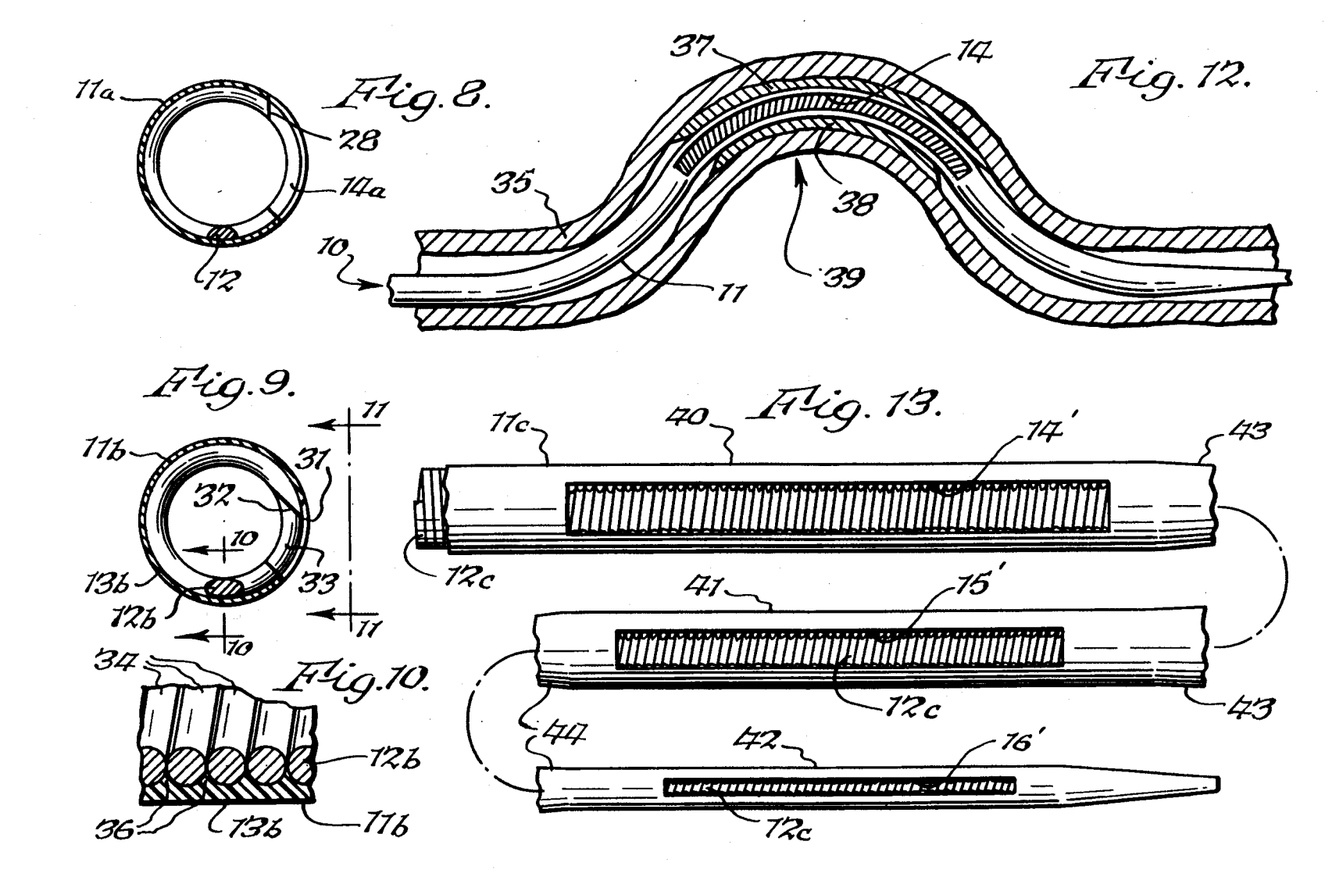
FIG. 8 is a cross sectional view similar to FIG. 5 but showing a different type of cutting edge formed on the catheter.
FIG. 9 is a cross sectional view similar to FIG. 5 but showing still another type of wire coil and casing construction which can provide a flexible catheter and also showing another type of cutting edge.
FIG. 10 is an enlarged fragmentary cross sectional view taken substantially along line 10—10 of FIG. 9 and showing the structure of the coil and the casing of the catheter.
FIG. 12 is a fragmentary cross sectional view showing the manner in which the catheter can conform to the curvature of a curved artery during the process of excising a lesion therein.
FIG. 13 is a fragmentary side elevational view similar to FIG. 4 and showing a modified form of catheter with a plurality of different sized cutting windows are located in the end thereof.

In FIG. 8, a catheter 11a is shown having a window 14a of a different cut. In this respect, as can be seen from a comparison of FIG. 5 with FIG. 8, the angle 28 of the cutting edge is different from the angle of cutting edge 18 of FIG. 5. This is the only difference. Otherwise, all parts of catheter 11a are identical to catheter 11.

Figures 11, 14, 15, 16, 17:
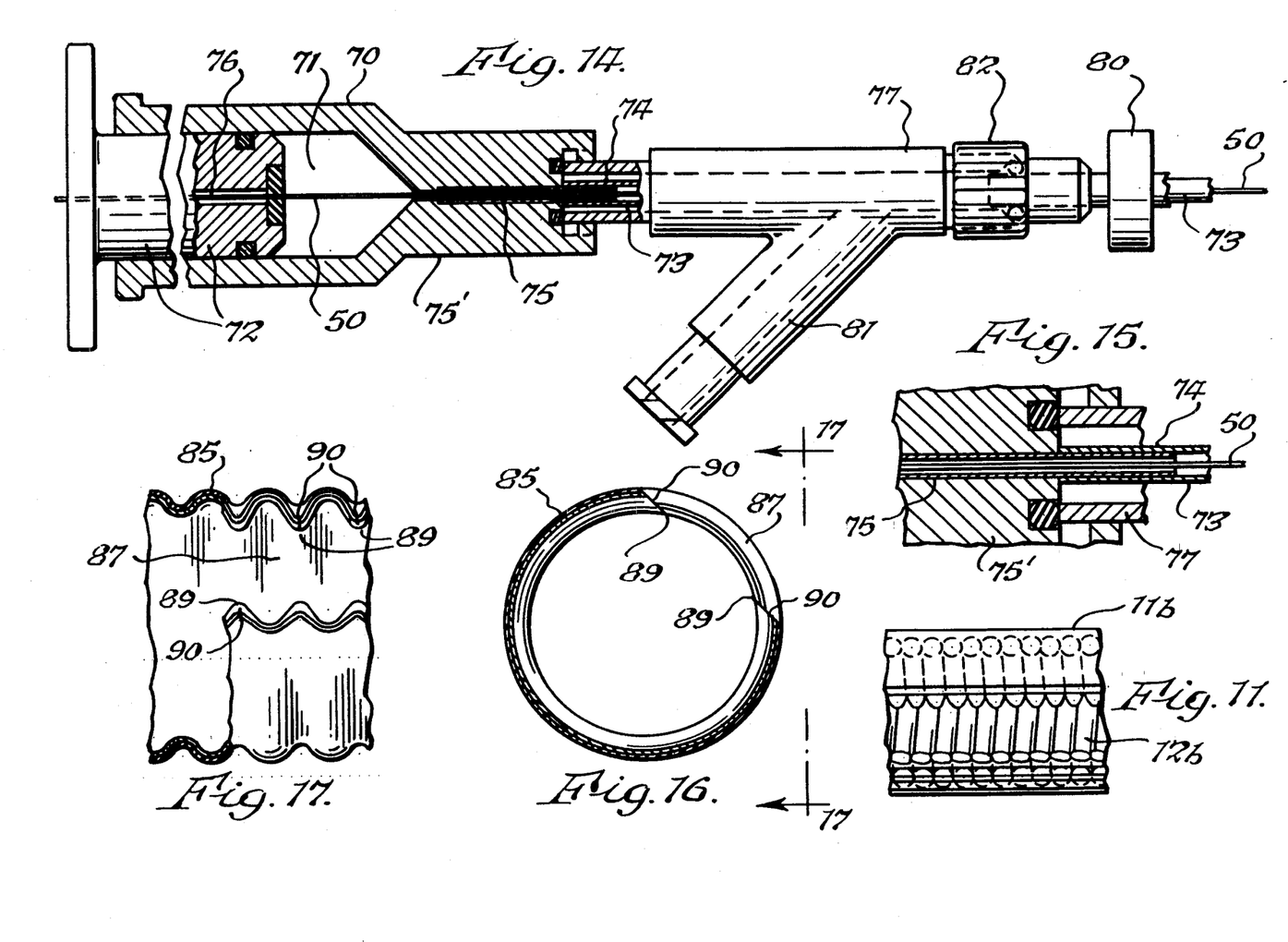

In FIGS. 9-11 a still further modified catheter 11b is shown. This catheter is identical in all respects to catheter 11 except that the cutting edge 31 in window 33 is formed so that the surface 32 is inclined as shown and the wire of coil 12b is not centerless ground and the casing 13b, which may be polyethylene, polypropylene or any other suitable material, is molded about the wire coil 12b (FIG. 10). In this embodiment the gauge is the thickness of casing 13b, that is, when the catheter is rotated within a vessel, the cutting edge 31 can get no closer to the wall of the vessel than the thickness of casing 13b.

In FIG. 10 the structure between coil 12b and casing 13b is shown. As can be seen, the casing, which is molded about coil 12, enters the valleys 36 between adjacent turns 34 to provide a good joint therebetween. It will be appreciated that the catheter is flexible because of the flexibility of the coil structure and the flexibility of the casing. Thus, the catheter can traverse bends in blood vessels and can cut lesions in such bends.

In FIG. 12 there is a representation of catheter 10 in a blood vessel 35 having a bend therein. As can be seen, there are lesions 37 and 38 at bend 39. When catheter 10 is rotated, the cutting edge in window 14 will cut lesions 37 and 38, and further, the catheter 10 will flex as it rotates so that the cutting edge within window 14 can effect a cutting action for a full 360°. Thus, the cutting edge can cut a lesion on the convex surface of a blood vessel on which lesion 38 is located as well as on the concave surface on which lesion 37 is located.

In FIG. 13 a modified catheter 11c is disclosed. This catheter has windows 14′ 15′ and 16′. The cutting edges within these windows can be the same as described above relative to FIGS. 4–7 or FIG. 8 or FIG. 9. The difference between the embodiment of FIG. 4 and the embodiment of FIG. 13 is that the end portion is not uniformly tapered but consists of a plurality of substantially cylindrical configurations 40, 41 and 42 which are connected by tapered portions. More specifically, tapered portion 43 connects portions 40 and 41, and tapered portion 44 connects portions 41 and 42. The coil is continuous, and it has portions of different constant diameters connected by tapered coil portions, and the wire is of constant diameter throughout the length of the coil.

The wires in the various embodiments may be of any suitable diameter which will provide the desired flexibility. Thus, for example, the wire sizes may range between 0.005 and 0.015 inches, but, as noted above, they may be of any suitable diameter. Preferably the wires are fabricated of stainless steel, but they may be fabricated of any other metal or plastic. Also, as noted above, the sheath 13 for the wire coil may be any flexible plastic including but not limited to polyethylene and polypropylene. The sheath may have any suitable thickness which will give the desired strength and flexibility. The outer diameter of the catheter may be that which is normally used, and it may vary, depending on the size of the arteries with which it is to be used.

The uniqueness of the above-described flexible catheter structure having a window extending through the coil and casing is due to a plurality of related factors. The first factor is that the flexibility of the catheter is obtained because of the flexibility of the coil and the flexibility of the casing surrounding the coil. The second factor is that the window is formed in the coil without causing the coil to fall apart. In fact even cutting a single wire of the coil would cause it to separate. However, the uniqueness of the combination of the coil and casing with a window therein is that the portion of the casing proximate the window holds the coil together in spite of its being cut. Certain embodiments of the catheter, namely, the above-described embodiments of FIGS. 4–13 are further unique in that the edge of the window in the coil also serves as a cutting blade. In the embodiments of FIGS. 18–22, to be described hereafter, the unique flexible windowed coil and casing are the basis for a catheter which utilizes an internal flexible cutter member which traverses the window.

The above-described atherectomy catheter 11 is shown in FIGS. 1, 2, 3, 14 and 15 as being used as part of an atherectomy catheter device 10 which includes a drive unit D and associated structure for guiding the catheter and supplying various liquids thereto during operation.

The atherectomy catheter 11 and associated tubing are introduced into a femoral artery in the same manner as a conventional "Simpson" type of atherectomy catheter having a rigid distal end, or in the same manner as an angioplasty balloon catheter. Briefly, an introducer sheath or pilot catheter 45 (FIG. 1) is introduced into the femoral artery the conventional manner. Thereafter, a guiding catheter 47 having the proper curvature at its distal end (not shown) is introduced through the pilot catheter, and it is progressed through the artery until its tip enters the coronary artery which is to be treated.

Figure 1:
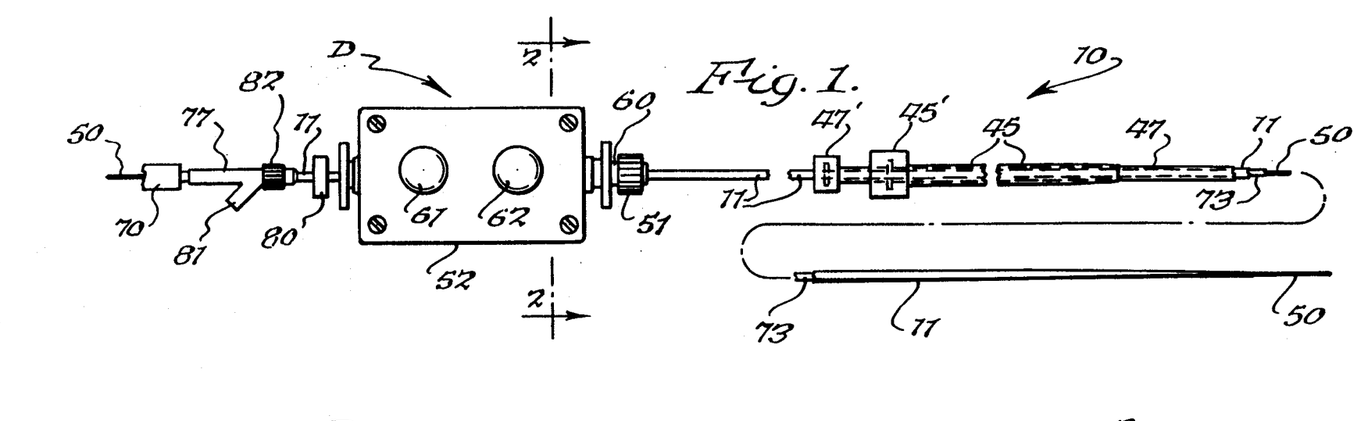
FIG. 1 is a fragmentary plan view of the improved atherectomy catheter device.

The end of the pilot catheter, which remains outside of the patient's body, is depicted by numeral 45′ and the portion of the guiding catheter 47, which remains outside of the patient's body, is depicted by the numeral 47′.

After guiding catheter 47 has been inserted as described above, an assembly consisting of drive motor D, atherectomy catheter 11, guide wire 50, dye-carrying lumen 73, rotatable hemostasis valve 80, fitting 77 and syringe 70 is utilized. The atherectomy assembly 10 includes the drive unit D having a rotatable tube 60 therein. The atherectomy catheter 11 (FIG. 2) extends through tube 60, as do the dye-carrying lumen 73 and the guide wire 50 therein. Attached to atherectomy catheter 11, at the left of drive unit D, are the rotatable hemostasis valve 80, the fitting 77, and the syringe 70. The atherectomy catheter 11, lumen 73 and guide wire 50 are axially movable through drive unit tube 60 during installation of the atherectomy catheter 11 into the patient's body.

Before the assembly containing the atherectomy catheter 11, dye-carrying lumen 73 and guide wire 50 are inserted into the guiding catheter 47, the atherectomy catheter 11 is flushed with saline solution which is injected through conduit 81 of fitting 77 by a suitable syringe (not shown). Also at this time plunger 72 is utilized to flush dye through lumen 73 (see FIG. 14). The flushing of catheter 11 and lumen 73 purges air therefrom. The guide wire 50 (FIGS. 14 and 15) protrudes out of the rear end of syringe 70, and it passes through tube 75 in the neck 75′ of the syringe and through tube 76 in the plunger 72 of the syringe. The dye-carrying lumen 73 has its proximal end 74 mounted on tube 75 and its distal end proximate the cutting window of catheter 11. Before the insertion of catheter 11 and lumen 73 and guide wire 50 into guiding catheter 47, guide wire 50 is grasped where it protrudes from the end of syringe 70, and it is withdrawn into the tip of the atherectomy catheter 11 so that it does not protrude therefrom. Then the atherectomy catheter 11, dye-carrying lumen 73, and guide wire 50 are progressed through the guiding catheter 47 until the distal tip of the atherectomy catheter 11 reaches the distal tip of guiding catheter 47 and is parked slightly before the entry to the coronary artery. The guide wire 50, which can be grasped where it protrudes from syringe 70, is then advanced into the coronary artery and articulated until it crosses the lesion which is to be excised. Catheter 11 is then advanced over the guide wire 50 to the lesion. At this time the tip of the atherectomy catheter 11 is at the proximal point of the lesion. It is not positioned with its window opposite the lesion. Dye is then injected into the lesion site by pushing plunger 72 of syringe 70 to cause dye to be ejected from syringe chamber 71, through dye-carrying lumen 73. All of the foregoing is effected by the use of fluoroscopy. The reason that the lumen 73 is used to deliver the contrast dye to the distal tip of catheter 11 is because there is a close fit between atherectomy catheter 11 and guiding catheter 47, and the space therebetween cannot be used to convey dye to the site of the lesion. This close fit is necessary for efficient linear movement of catheter 11. In this respect, if there was looseness between catheters 11 and 47, the subsequently discussed reciprocatory motion imparted by drive motor D would not be accurately realized at the distal end of catheter 11.

Figure 3:
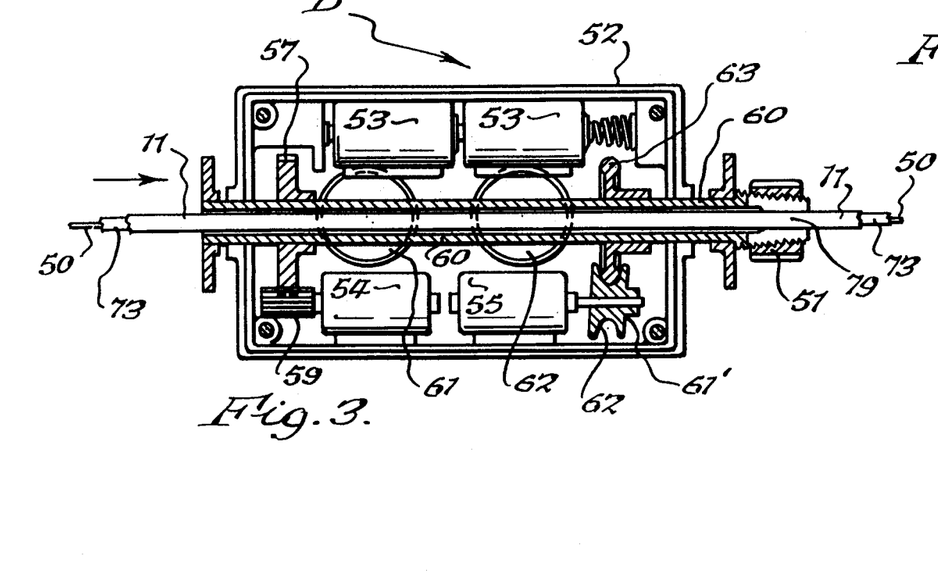
FIG. 3 is a cross sectional view taken substantially along line 3—3 of FIG. 2.

While the tip of catheter 11 is positioned at the proximal area of the lesion, drive motor D is advanced over catheter 11 toward the end 47' of guiding catheter 47, leaving a space of about 2 inches therebetween. This is possible because catheter 11 fits loosely in tube 60 of motor D. Chuck 51 of tube 60 is then tightened around the portion 79 of catheter 11 (FIG. 3). Drive unit D is then held and activated to rotate and reciprocate tube 60 and atherectomy catheter 11 connected thereto by chuck 51. The catheter 11 is then pushed slowly into the guiding catheter 47 to cause the end of atherectomy catheter 11 to mechanically dilitate the lesion and the artery. The lesion is then forced into the rotating cutting window of catheter 11, and the serrated knife edge on the cutting window, during rotation and reciprocation, slices a thin ribbon of lesion material therefrom. At this point it is noted that the tapered end, such as 22' of the atherectomy catheter, effects the dilitation of the lesion. After the non-tapered portion of the catheter reaches the lesion, it produces the maximum amount of cutting. The lesion material is aspirated through catheter 11 by applying a suction at conduit 81 of fitting 77.

Figure 2:
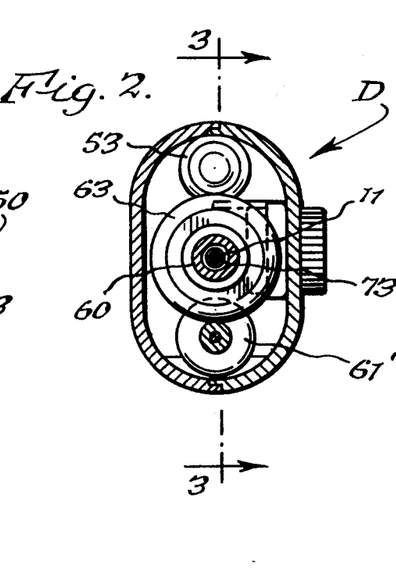
FIG. 2 is an enlarged cross sectional view taken substantially along line 2—2 of FIG. 1 and showing a portion of the motor drive unit for the catheter.

Driving device D includes a casing 52 housing batteries 53 which are coupled to motors 54 and 55. Motor 54 drives gear 57 through pinion 59, and gear 57 is keyed to tubular member 60 on which chuck 51 is mounted. A potentiometer 61 actuates motor 54 at various speeds. Thus, when motor 54 is actuated, catheter 11 will be rotated.

The driving device D also has a potentiometer 62 which actuates motor 55 at various speeds to drive wabble wheel 61' having a groove 62 therein. A circular disc 63 is keyed to hollow shaft 60 and its outer edge rides in groove 62. Thus when motor 55 is actuated, hollow shaft 60 will be caused to reciprocate, and thus atherectomy catheter 11 will also reciprocate, as noted above, in addition to rotating. When the atherectomy catheter 11 reciprocates, the teeth, such as 19, will be moved back and forth across the lesion to effect a cutting action. As noted above, during the cutting action, aspiration is applied to duct 81 of fitting 77 to move excised material within atherectomy catheter 11 proximally and away from the cutting window for safe storage or complete removal of lesion material. Rotating hemostasis valve 80 which is located between fitting 77 and drive motor D permits catheter 11 to be rotated by motor D without requiring the syringe 70 and fitting 77 to be rotated.

As noted above, the distal end of the atherectomy catheter is tapered. Thus, the proper diameter portion can be positioned at the site of the lesion. It will also be appreciated that the distal end may have only a single relatively short window therein and that different diameter catheters of this type can be used for different size blood vessels.

In FIGS. 16 and 17 an alternate type of flexible atherectomy catheter is shown which is fabricated from a corrugated tube 85 having a window 87 therein with cutting edges 89 on the edge portions 90 of the window. Corrugated tube 85 may be fabricated out of any suitable material, either plastic or metal.

Figure 18:
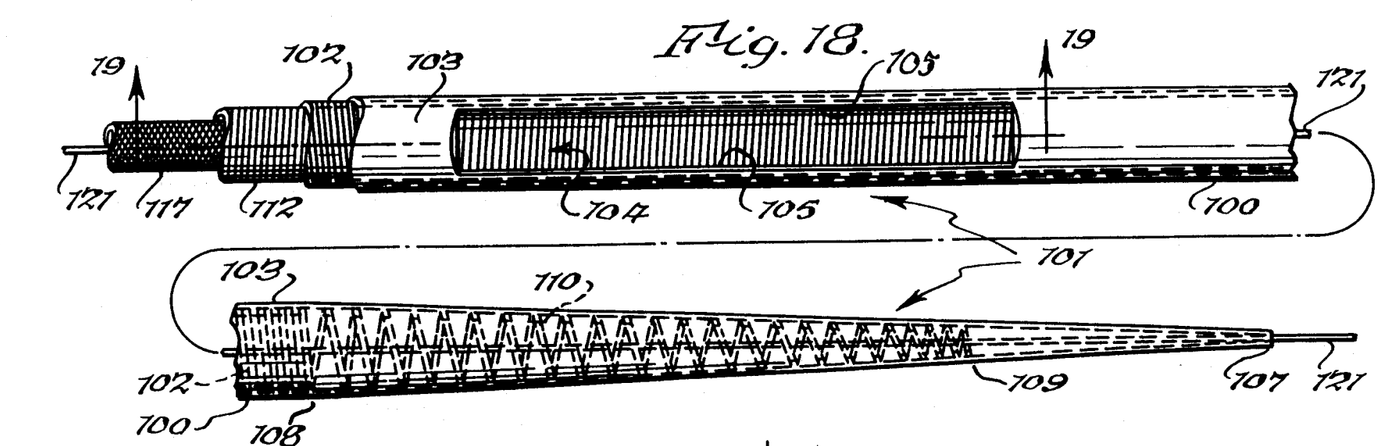
FIG. 18 is a fragmentary view of a modified embodiment of the present invention.
Figure 19:
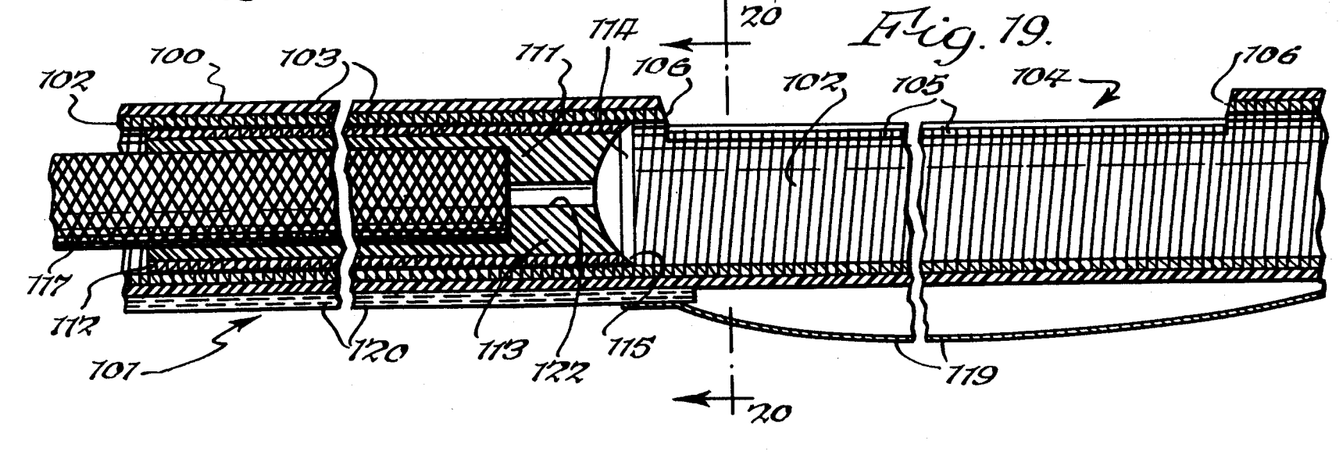
FIG. 19 is a fragmentary enlarged cross sectional view taken substantially along line 19—19 of FIG. 18.
Figure 20:
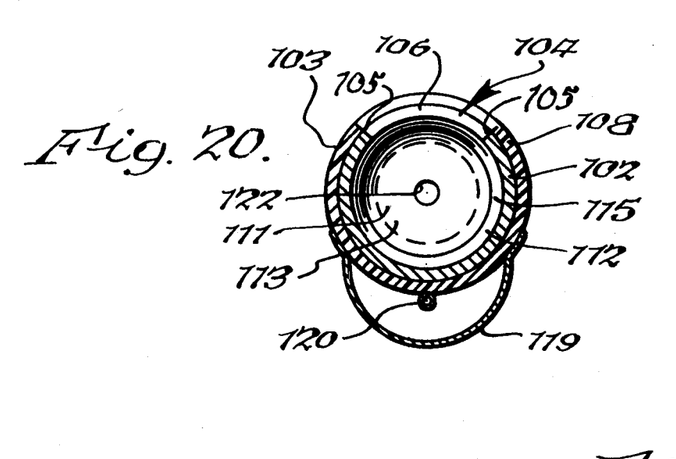
FIG. 20 is a cross sectional view taken substantially along line 20—20 of FIG. 19.

In FIGS. 18-20 another embodiment of the present invention is disclosed which utilizes a sheathed coil for imparting flexibility to the catheter. The distal end 200 of catheter 101 comprises a flexible coil 102 of wire or plastic which is encased by a sheath 103 of suitable flexible plastic. A window or opening 104 extends through both the sheath 203 and coil 102. The edges 105 of window 104 are cut in a radial direction and do not comprise cutting surfaces. The coil 102 is fabricated of flat wire and thus there are no teeth at edges 105, and thus there will be no serrations which could provide cutting edges as described above relative to the embodiment of FIG. 6. The ends 106 of the window 104 are cut at a slight angle. The coil 102 and sheath or casing 103 are of uniform diameter past window 104, and they both gradually taper from an area 108 to the end 107 of the catheter. From the area 108, the coil, which is continuous, is tapered and wound at the pitch shown in the zone 110 between areas 108 and 109. The tapered portion of the catheter between areas 107 and 109 comprises only the flexible plastic sheath.

A flexible cutter assembly or excising member 111 is mounted for axial and rotary movement within wire coil 102 and past window 104. The cutter assembly 111 includes an outer coil of flexible flat wire 112 which is mounted on a flexible annular plastic member 113. The edge 114 of wire coil 112 is sharpened to provide a cutting edge at 115. Annular plastic member 113 is firmly secured to flexible braided wire cable 117, and when cable 117 is rotated by a motor at the proximal end of the catheter 101, the excising member 111 will be caused to rotate, and when cable 117 is advanced to the right in FIG. 19, the excising member 111 will flex as the casing 103 and coil 102 flex, and the knife edge 115 will traverse window 104 to cut any lesion which enters the window as a result of the inflation of balloon 119 through duct 120, as in the prior art. A wire 121 passes through the hollow cable 117 and through hole 122 of plastic member 113 from the proximal end of the catheter, and the wire is either maintained within end 107 of the catheter or can be pushed out therefrom during operation, as explained above relative to FIG. 14. Lesion material cut from the vessel is stored in the tapered lumen area between 108 and 109.

Figure 21:
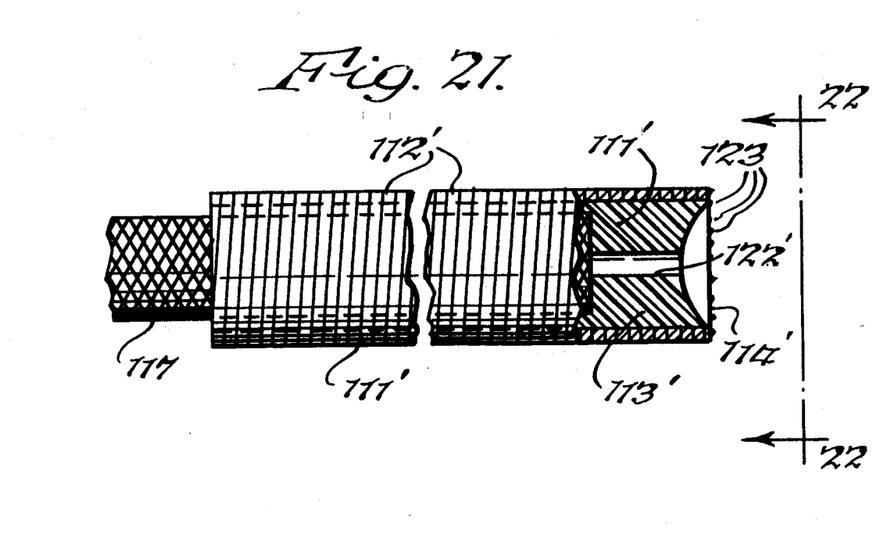
FIG. 21 is a fragmentary view, partially in cross section of a modified excising member which can be used in the embodiment of FIGS. 18-20.
Figure 22:
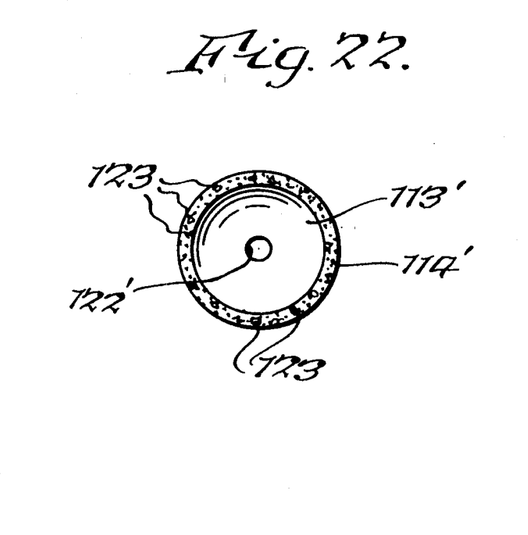
FIG. 22 is an end elevational view taken substantially in the direction of arrows 22—22 of FIG. 21.

A modification of the embodiment of FIGS. 18–20 is shown in FIGS. 21 and 22, the only difference being in the shape of the cutting edge of the cutter assembly which is now designated 111' which includes an outer flat flexible wire coil 112' which is firmly attached to a flexible plastic member 113' with hole 122' therein which in turn is secured to cable 117. The only difference between the cutter assemblies 111 and 111' is in the face of the cutting edge 114' which is the full radial dimension of the flat wire of coil 112' and which includes on the face thereof a deposit of abrasive material 123 which can be diamonds or other abrasive material. Thus, when the cutter assembly 111' is rotated and advanced through window 102, the cutting edge 114' will abrade lesion material with which it comes into contact.

In all embodiments of the present invention, the coil member with a plastic sheath which comprises the flexible cutting portion of the catheter need only be the last few inches of the entire catheter, and the remainder of the catheter which extends back toward the driving motor need be only ordinary flexible tubing to which the coiled sheathed cutting portion is attached.

While preferred embodiments of the present invention have been disclosed, it will be appreciated that it is not limited thereto but may be otherwise embodied within the scope of the following claims.

What is claimed is:

1. An atherectomy catheter comprising elongated flexible tubular means having a longitudinal axis and a circumference for placement next to a lesion in a blood vessel, window means defining an opening of less than 360 degrees in said circumference of said elongated flexible tubular means for receiving said lesion, a flexible edge portion on said window means, flexible cutting edge means on said flexible edge portion for flexing with the curvature of said blood vessel and for excising said lesion which enters said window means, said elongated tubular means comprising a flexible helical coil member, said flexible cutting edge means comprising exposed adjacent severed ends of said flexible coil member, and a flexible casing on said flexible coil member for retaining said coil member in assembled relationship at said window means.

2. An atherectomy catheter as set forth in claim 1 wherein said flexible cutting edge means is serrated.

3. An atherectomy catheter as set forth in claim 1 wherein said flexible coil member has inner and outer surfaces, and wherein said flexible cutting edge means is located at said inner surface of said flexible coil member.

4. An atherectomy catheter as set forth in claim 1 wherein said flexible coil member has inner and outer surfaces, and wherein said flexible cutting edge means is located at said outer surface of said flexible coil member.

5. An atherectomy catheter as set forth in claim 1 including means for rotating said tubular means.

6. An atherectomy catheter as set forth in claim 5 including means for reciprocating said tubular means.

7. An atherectomy catheter as set forth in claim 6 wherein said cutting edge means is serrated.

8. An atherectomy catheter as set forth in claim 7 wherein said cutting edge means has an uniform serration, and wherein the distance of said reciprocation is greater than the pitch of said uniform serration.

9. An atherectomy catheter as set forth in claim 1 including means for rotating said elongated flexible tubular means at a selectively variable speed.

10. An atherectomy catheter as set forth in claim 9 including means for reciprocating said elongated flexible tubular means at a selectively variable speed.

11. An atherectomy catheter as set forth in claim 10 wherein said selectively variable speeds can be held at constant speeds.

12. An atherectomy catheter as set forth in claim 1 including means for reciprocating said elongated flexible tubular means.

13. An atherectomy catheter as set forth in claim 1 including an elongated flexible guide member within said tubular means.

14. An atherectomy catheter as set forth in claim 1 including means for conducting fluid into said elongated flexible tubular means.

15. An atherectomy catheter as set forth in claim 14 including means for withdrawing fluid from said elongated flexible tubular means.

16. An atherectomy catheter as set forth in claim 1 including means for applying suction to said elongated flexible tubular means.

17. An atherectomy catheter as set forth in claim 16 including means for conducting fluid into said elongated flexible tubular means.

18. An atherectomy catheter as set forth in claim 1 including, a second opening in said casing, a dye-carrying lumen in said coil, a guide wire in said lumen, a drive motor for reciprocating and rotating said atherectomy catheter, and means for injecting dye into said dye-carrying lumen.

* * * * *

UNITED STATES PATENT AND TRADEMARK OFFICE
CERTIFICATE OF CORRECTION

PATENT NO. : 5,366,464
DATED : November 22, 1994
INVENTOR(S) : John C. Belknap

It is certified that error appears in the above-identified patent and that said Letters Patent is hereby corrected as shown below:

Column 1, line 28, after "conform" insert --to--.

Column 5, line 64, after "artery" insert --in--.

Column 7, line 62, change "200" to --100--;
         line 66, change "203" to --103--.

Signed and Sealed this

Twenty-fourth Day of January, 1995

*Attest:*

BRUCE LEHMAN

*Attesting Officer*      *Commissioner of Patents and Trademarks*